(12) United States Patent
Gougeon et al.

(10) Patent No.: US 7,648,961 B2
(45) Date of Patent: Jan. 19, 2010

(54) USE OF SOMATOSTATIN OR ONE OF ITS ANALOGUES FOR PREPARING A MEDICAMENT INTENDED TO REGULATE THE OVARIAN FOLLICULAR RESERVE IN NON-MENOPAUSAL WOMEN

(75) Inventors: Alain Gougeon, Chaponost (FR); Ernest Loumaye, Massongy (FR)

(73) Assignee: Preglem S.A., Plan-Les-Quates (CH)

( * ) Notice: Subject to any disclaimer, the term of this patent is extended or adjusted under 35 U.S.C. 154(b) by 156 days.

(21) Appl. No.: 10/575,236

(22) PCT Filed: Oct. 8, 2004

(86) PCT No.: PCT/FR2004/002536

§ 371 (c)(1), (2), (4) Date: Nov. 16, 2006

(87) PCT Pub. No.: WO2005/034989

PCT Pub. Date: Apr. 21, 2005

(65) Prior Publication Data

US 2007/0155659 A1 Jul. 5, 2007

(30) Foreign Application Priority Data

Oct. 10, 2003 (EP) .................................. 03292505

(51) Int. Cl.
*A61K 38/12* (2006.01)
(52) U.S. Cl. ........................ 514/11; 530/317; 530/311
(58) Field of Classification Search ........................ None
See application file for complete search history.

(56) References Cited

U.S. PATENT DOCUMENTS 6,362,164 B1 * 3/2002 Weckbecker .................. 514/16

FOREIGN PATENT DOCUMENTS

| WO | WO 97/01579 | 1/1997 |
| WO | WO 01/96393 A2 | 12/2001 |
| WO | WO 02/10192 | 2/2002 |
| WO | WO 02/072602 | 9/2002 |
| WO | WO 02/072602 A2 * | 9/2002 |

OTHER PUBLICATIONS

Terzolo, 2000, The Journal of Clinical Endocrinology and Metabolism, 85, 1310-1315.*
Baumbach, 1998, Molecular Pharmacology, 54, 864-873.*
Hepplemann, 1999, Neurosciences letters, 259, 62-64.*
Poitout, 2001, J. Med. Chem., 44, 2990-3000.*
Wermuth, Pure and Appl. Chem, 1998, 70, 1129-1143.*
Nilsoson Eric, Ph.D., DVM and Michael K. Skinner, Ph.D., Cellular interactions that control primoridal follicle development and folliculogenesis, US National Library of Medicine (NLM), Bethesda, MD, US; The Society of Gynecologic Investigation; pp. S17-S20, Jan. 2001.
Maclachlan et al., A Controlled Study of Luteinizing Hormone-Releasing Hormone Agonist (Buserelin) for the Induction of Folliculogenesis before In Vitro Fertilization, New England Journal of Medicine; 320:19, 1233-7, 1989.
Van Der Meer et al., , Octreotide, a somatostatin analogue, alters ovarian sensitivity to gonadotrophin stimulation as measured by the follicle stimulating hormone threshold in polycycstic ovary syndrome, European Society for Human Reproduction and Embryology; vol. 13, No. 6, pp. 1465-1469, 1998.
Reubi et al., A new peptidic somatostatin agonist with high affinity to all five somatostatin receptors, European Journal of Pharmacology 456, pp. 45-49, 2002.

* cited by examiner

*Primary Examiner*—Andrew D Kosar
*Assistant Examiner*—Satyanarayana R Gudibande
(74) *Attorney, Agent, or Firm*—Hunton & Williams LLP

(57) ABSTRACT

The invention primarily relates to the use of somatostatin or one of the agonistic analogs thereof for producing a medicament serving to regulate the ovarian follicular reserve and, in particular, to reduce the depletion of the ovarian follicular reserve over time in non-menopausal women or to the use of an antagonistic analog of somatostatin for producing a medicament serving to accelerate the start of growing of quiescent follicles in non-menopausal women. The invention also relates to in vitro applications of somatostatin and of agonistic and antagonistic analogs thereof.

5 Claims, 3 Drawing Sheets

USE OF SOMATOSTATIN OR ONE OF ITS ANALOGUES FOR PREPARING A MEDICAMENT INTENDED TO REGULATE THE OVARIAN FOLLICULAR RESERVE IN NON-MENOPAUSAL WOMEN

FIELD OF INVENTION

The invention relates to the use of somatostatin or one of its agonist analogues for preparing a medicament intended to regulate the ovarian follicular reserve in non-menopausal women, or the use of a somatostatin antagonist analogue for preparing a medicament intended to accelerate the start of growth of the quiescent follicles in non-menopausal women. The invention also relates to the in vitro use of somatostatin or one of its agonist analogues in order to inhibit the start of growth of quiescent follicles in ovarian tissue, or the in vitro use of a somatostatin antagonist analogue in order to accelerate the start of growth of quiescent follicles in ovarian tissue.

BACKGROUND OF INVENTION

In women, as in all mammals, fertility is dependent on the presence in the ovaries of female gametes called "oocytes". In humans, the oocyte capital is constituted once and for all at birth; the number of oocytes is then comprised between 500 000 and 1 million per ovary. These oocytes are surrounded by a few granulosa cells; this functional group is called an ovarian follicle (Gougeon, A., *Endocrine Reviews* (1996),17, 121-155). At birth, but also throughout life until menopause, the majority of the ovarian follicles are in a dormant state.

From its constitution, the oocyte capital progressively diminishes: thus, there are approximately 200 000 follicles per ovary at puberty, approximately 80 000 at 20 years of age, approximately 30 000 at 30 years of age, approximately 10 000 at 40 years of age, the capital being practically depleted at around 50 years of age (cf. Gougeon, A. and Lefevre, B., <<Folliculogénèse et maturation ovocytaire>> in *Médecine de la reproduction*, $3^{rd}$ edition, Ed. Flammarion, p. 49). The depletion of the oocyte capital corresponds clinically to menopause. The dormant follicles present in the ovary at a given time constitute the "ovarian reserve".

Two mechanisms are involved in the progressive depletion of the ovarian reserve. Approximately 80% of the follicles disappear at the start of apoptosis, while the remaining 20% start to grow. The latter then begin a long process of development (approximately 6 months) in which a minority of them (approximately 400 over a lifetime) will arrive at the stage of preovulatory follicles containing a mature oocyte which is able to be to be fertilized (Gougeon, A., *Endocrine Reviews* (1996), 17, 121-155). The majority of the growing follicles disappear through apoptosis leading to their involution; apoptosis strikes them at any stage of their development.

The change from the quiescent follicle stage to the growing follicle stage is a phenomenon which is continuous but of variable intensity. In particular, it accelerates in the 10 to 15 years preceding menopause, from approximately 38 years of age.

The factors stimulating the first stages of growth (starting from the large primary follicle) are relatively well known. They include gonadotropins (LH and FSH) but particularly growth factors and steroids such as androgens. However, the mechanisms controlling the initiation of follicle growth are not well known. It is well established that this stage of folliculogenesis is not dependent on gonadotropins (LH and FSH) (cf. for example Bullun, S. and Adashi, E., *Williams Textbook of Endocrinology*, Tenth Edition (2003), 587-664). A hormone known as AMH (Anti-Mullerian hormone) could be involved in maintaining the quiescence of the follicles while a peptide known as Kit-Ligand (also called SCF) could be involved in activating the growth of dormant follicles. In addition, a growth factor known as GDF-9 seems to be important for maintaining the growth once it is triggered.

Somatostatin (SST) is a cyclic peptide present in two forms in the organism, one form containing 14 amino acids and one form containing 28 amino acids. The biological activity of these two forms of SST is similar. The SST-14 form is the predominant form in the central nervous system. It inhibits the secretion of the growth hormone by the somatotrope cells of the anterior pituitary. The SST-28 form is preferably expressed in the stomach and the pancreas. The biological activity of SST is induced by means of a series of membrane receptors coupled with a protein G, 5 sub-types of which have been characterized, namely the sub-types SSTR1 to SSTR5 (Reubi, J. C., *Cancer Res.*, 47, 551-558; Resine, T., et al., *Endocr. Review*, 16, 427-442; Lamberts, SW. et al., *Endocr. Review*, 12, 450-482).

The presence of SST in the ovary has been demonstrated in several species including pigs (Mori, T. et al., *Acta Endocrinol.* (Copenh.) (1984), 106(2), 254-259), rats (McNeill, D. L. et al., *Am. J Anat.* (1987), 179(3), 269-76) and in women (Holst et al., *Hum. Reprod.* (1994), 9(8), 1448-1451). SST receptors have been identified in the ovary of the rat (Lidor, A. et al., *Gynecol. Endocrinol.* (1998), 12(2), 97-101) as well as in the human ovary in particular the sub-types 1, 2A and 5 (Strauss et al., *Hum. Reprod.* (2003), 18, Suppl. 1, P-495).

The contribution of SST in ovarian physiology has been studied by several authors. In rats, the in vivo administration of SST seems to reduce the number of pituitary cells producing LH and FSH as well as the number of preovulatory follicles in the ovary (Nestorovic et al., *Histochem. J.* (2001), 33(11-12), 695-702). In vitro, SST inhibits aromatase and the production of progesterone, stimulated by FSH, in a model of granulosa cells (Andreani, C. L. et al., *Hum. Reprod.* (1995), 10(8), 1968-1973). In pigs, SST inhibits the increase in cAMP induced by LH and forskolin in the granulosa cells (Rajkumar, K. et al., *J. Endocrinol.* (1992), 134(2), 297-306), and seems to inhibit the nuclear maturation of the preovulatory oocyte (Mori, T. et al., *Acta Endocrinol.* (Copenh.) (1985), 110(3), 408-412). In women, in vitro studies on granulosa cells from preovulatory follicles suggest a direct role of SST in inhibiting the synthesis of IGF-BP1 and of progesterone (Holst, N. et al., *Fertil. Steril.* (1997), 68(3), 478-482). In women, in vivo, SST is capable of reducing the secretion of LH by the pituitary, reducing the production of androgens and the IGF-1 serum levels. By contrast, SST increases the serum levels of IGF-BP3 (Fulghesu, A. M. et al.,

*Fertil. Steril.* (1995), 64(4), 703-708; Piaditis, G. P. et al., *Clin. Endocrinol.* (Oxf.) (1996), 45(5), 595-604). SST was co-administered with FSH during treatment to induce ovulation in patients who are infertile as a result of a polycystic ovary syndrome. The capacity of SST to reduce the LH serum levels, and to reduce the serum levels of growth hormone and of IGF-I has been confirmed. This endocrine effect is not however accompanied by a significant impact on the follicle growth induced by the administration of FSH (Lidor, A. et al., *Gynecol. Endocrinol.* (1998), 12(2), 97-101; van der Meer, M. et al., *Hum. Reprod.* (1998), 13(6), 1465-1469). In summary, until now a marginal effect of SST on the pituitary secretion of LH and on the production of progesterone by the granulosa cells of preovulatory follicles has been reported.

BRIEF SUMMARY OF THE INVENTION

The applicants have now discovered, in a surprising manner, that SST and its analogues have the capacity to inhibit the transition of the follicles from a quiescent stage to a growth stage and that this faculty allows new therapeutic uses for these compounds.

The benefit of this discovery resides primarily in the possibility of using SST or an SST agonist analogue for preparing a medicament intended to diminish or inhibit the start of growth of follicles in the quiescent stage. Secondly, it is also possible to use an antagonist analogue of this peptide in order to prepare a medicament intended to accelerate the start of growth of the quiescent follicles.

There exists a set of clinical situations for which it would be desirable from a medical perspective for the patient to slow the use of the ovarian reserve in order to delay the depletion of the latter and therefore to preserve the ovarian function and fertility. These situations are typically, and in a non-exclusive manner, patients at risk of early menopause. It is well known that certain patients have premature depletion of their follicular capital. Menopause then occurs before 40 years of age and sometimes even before thirty years of age. It is often possible to predict this early menopause on the basis of family antecedents, or genetic anomalies such as Turner syndrome (complete or partial). In this situation, the administration of SST or of one of its agonist analogues is a preventive measure and aims to slow the start of growth of the quiescent follicles.

The same applies for patients having difficulty conceiving and for whom the chronological age or biological age of their ovaries corresponds to the period of acceleration of activation of the quiescent follicles: slowing this depletion of follicular capital should make it possible to increase the efficiency of the treatments and the chances of becoming pregnant.

Another clinical situation which may benefit from a treatment by SST or by one of its agonist analogues is the graft (preferably an autograft) of an ovary or of ovary fragments. In this context, the resumption of ovarian function is often temporary and is accompanied by a premature depletion of the number of primordial follicles (Baird, D. T. et al., *Endocrinology* (1999), 140, 462-471). It has in fact been demonstrated that, during the transplantation, the granulosa cells of the growing follicles are more inclined to start apoptosis than those of the primordial follicles (Liu, J. et al., *Hum. Reprod.* (2002), 17, 605-611). Moreover, the removal of ovarian tissue and its fragmentation causes the primordial follicles to move rapidly and en masse toward a stage of late primary follicles (cf. Wandji S-A, et al., *Hum. Reprod.* (1997), 12, 1993-2001; cf. also the control group of the example of the present application).

In the context of this application, somatostatin agonist analogues (or somatostatin) can be added to the various media for sampling, washing, preserving, freezing and thawing of ovarian tissue for the purpose of grafts. The invention therefore also relates to the corresponding media comprising a somatostatin agonist analogue. It also relates to the use of a somatostatin agonist analogue as a protective adjuvant for the media for sampling, washing, preserving, freezing and thawing of ovarian tissue.

Moreover, the in vitro use of somatostatin or of somatostatin agonist analogues can also be useful in the field of toxicological analyses and in the in vitro production of mature oocytes from fresh or frozen ovarian tissue. As regards the former, during tests of the effect of new chemical entities on ovarian follicles and their growth, the addition to the follicle sample of a somatostatin agonist analogue makes it possible to slow the follicle growth and thus to more easily observe any effect of acceleration of said growth caused by said new chemical entities. The addition of somatostatin antagonist makes it possible to move the follicular reserve towards the growth phases and to better evaluate the impact of new chemical entities on this phenomenon. As regards the in vivo production of mature oocytes, the addition to the follicle sample of a somatostatin agonist analogue allows the follicle growth to be slowed during the initial phase of culture. The addition of somatostatin antagonist in a second phase subsequently allows the follicular reserve to be moved toward the growth phases allowing a greater number of mature follicles and therefore of fertilizable oocytes to be obtained.

The use of somatostatin agonist analogues (or of somatostatin) in patients with polycystic ovaries is also beneficial. In fact, numerous observations suggest that polycystic ovaries have an abnormally high follicle population (cf. Hughesdon, *Obstet. Gynecol. Surv.* (1982), 37(2), 59-77). The excessive production of androgens by these follicles in an excessive quantity could be the origin of the metabolic and endocrine disorders observed in these patients. Moreover, a significant reduction of this follicle population by ovarian resection, cauterization or ultraviolet radiation, constitutes one of the most effective therapies because it allows the patients to ovulate at approximately 80% and to become pregnant at a cumulative rate of 75% over 18 months. Thus, the regular administration of a somatostatin agonist analogue (or of somatostatin) should bring about a reduction in the number of growing follicles and therefore of the supernumerary antral follicles producing androgens resulting in the resumption of fertile ovulatory cycles of a temporary or permanent nature.

Moreover, the use of somatostatin agonist analogues (or of somatostatin) in patients who are about to have, are currently having or have had chemotherapy or irradiation (for therapeutic or other purposes) reduces the risk of early menopause by preventing the accelerated activation of the follicular reserve which would make it more sensitive to the chemotherapy agents or to the ionizing radiation.

Other applications can also be envisaged, in particular in the veterinary field. The invention could be used to save species, the use of somatostatin agonist analogues (or of somatostatin) allowing the ovarian reserve of females to be preserved. Similarly, somatostatin antagonist analogues can be used in the context of in vitro or in vivo fertilizations in animals of high commercial value. Such animals with high commercial value can in particular be horses, bovines, ovines or goats; they can also be animals of transgenic origin.

In addition to the pathologies mentioned above, a systematic slowing of the depletion of the ovarian reserve could be envisaged in women not suffering from any ovarian dysfunction. In industrialized countries, the continuous extension of life expectancy (currently approximately 83 years in France) is accompanied by an extension of the post-menopausal period and of the problems associated with it: cardiopathies, osteoporosis, cutaneous aging, etc. Doubts are raised as to the long-term safety of hormonal substitute treatments for menopause. An attractive alternative would consequently be delaying the age at which menopause occurs. This would thus reduce the post-menopausal period and the associated risks. This delay would not however mean that fertility could be maintained up to 60 plus years of age. Numerous works suggest that ovarian function is maintained as long as a minimum number of follicles of the reserve is maintained, and that despite a "normal" ovarian function (steroid levels barely affected), the chances of pregnancy are extremely low.

In situations where it is sought to slow the use of the ovarian reserve, according to the invention natural somatostatin (SST14 or SST28), or, preferably, a somatostatin agonist analogue (natural or synthetic), will be used. The somatostatin agonist analogue can be a cyclic or non-cyclic polypeptide, a fusion or recombination protein, a non-peptidic chemical entity (i.e. peptidomimetic) or also an "SS-like" peptide such as corticostatin. The agonist analogues to be used must have high affinity for the SST receptor and induce a functional activity thereof such as the inhibition of the secretion of growth hormone by pituitary somatotrope cells and/or the inhibition of the in vitro proliferation of pituitary adenoma cells. Preferably, the somatostatin agonist analogue has high affinity for all or at least 2 or 3 of the sub-types of SST receptors or a greater affinity for at least one of the sub-types 1, 2, 3, 4 and 5 (for example for sub-type 2).

Agonist analogues of somatostatin have been described in particular in the patent application PCT WO 01/00676 or WO 98/08528 or also in the patents U.S. Pat. Nos. 6,387,932, 6,268,342, 6,057,338, 6,025,372.

DETAILED DESCRIPTION OF THE INVENTION

According to a particular variant of the invention, the somatostatin agonist analogues are compounds of general formula (I)

(I)

in which:
$X_1$ is a radical of formula (a) or (b)

$R_1$ independently representing each time it occurs an optionally substituted phenyl radical in which the optional substituents are independently chosen from a halogen atom and the methyl, ethyl, methoxy and ethoxy radicals, $R_2$ representing —$Z_1$—$CH_2$—$R_1$, —$CH_2$—CO—O—$CH_2$—$R_1$, $Z_1$ being O or S;
$X_2$ is an α-amino acid having an aromatic residue on the side chain $C_\alpha$, or an amino acid unit chosen from Dab, Dpr, Dpm, His, (Bzl)HyPro, thienyl-Ala, cyclohexyl-Ala and t-butyl-Ala;
A is a divalent residue chosen from Pro, $R_3$ is $NR_8R_9$—$C_{2-6}$alkylene, guanidino-$C_{2-6}$alkylene or $C_{2-6}$alkylene-COOH, $R_{3a}$ is H, $C_{1-4}$alkyl or has, independently, one of the meanings given for $R_3$, $R_{3b}$ is H or $C_{1-4}$ alkyl, $R_a$ is OH or $NR_5R_6$, $R_b$ is —$(CH_2)_{1-3}$— or —CH$(CH_3)$—, $R_4$ is H or $CH_3$, $R_{4a}$ is benzyl optionally substituted on the aromatic ring, each of $R_5$ and $R_6$ is independently H, $C_{1-4}$alkyl, ω-amino-$C_{1-4}$alkylene, ω-hydroxy-$C_{1-4}$alkylene or acyl, $R_7$ is a direct bond or $C_{1-6}$alkylene, each of $R_8$ and $R_9$ is independently H, $C_{1-4}$alkyl, ω-hydroxy-$C_{2-4}$alkylene, acyl or $CH_2OH$—$(CHOH)_c$—$CH_2$— in which c is 0, 1, 2, 3 or 4, or $R_8$ and $R_9$ form together with the nitrogen atom to which they are attached a heterocyclic group which can include an additional heteroatom, and $R_{11}$ is benzyl optionally substituted on the aromatic ring, —$(CH_2)_{1-3}$—OH, $CH_3$—CH(OH)— or —$(CH_2)_{1-5}$—$NR_5R_6$, and $ZZ_a$ is a natural or unnatural α-amino acid unit;

it being understood that $X_1$, $X_2$ and Lys each have the configuration L;

or are pharmaceutically acceptable salts or protected forms of compounds of general formula (I).

$ZZ_a$ can have a configuration D or L. $ZZ_a$ can be for example Thr, Ser, Ala, Val, Ile, Leu, Nle, His, Arg, Lys, Nal, Pal, Tyr, Trp, Phe substituted on the aromatic ring or $N^α$-benzyl-Gly. When $ZZ_a$ is Phe, its benzene ring can be substituted for example by $NH_2$, $NO_2$, $CH_3$, $OCH_3$ or a halogen atom, preferably in position para. When $ZZ_a$ is Phe, its benzene ring is preferably not substituted.

When A comprises a Pro amino acid residue, any substituent present on the proline ring, for example $R_3$—NH—CO—O— etc., is preferably in position 4. Such substituted proline residues can be in the cis form, for example such as in the trans form. Each geometric isomer individually as well as mixtures of these isomers are included in the uses according to the invention.

When A is in which $NR_8R_9$ forms a heterocyclic group, said group can be aromatic or saturated and can include a nitrogen atom or a nitrogen atom and a second hetero atom chosen from nitrogen and oxygen. Preferably, the heterocyclic group is for example pyridyl or morpholino. The $C_{2-6}$alkylene radical in this residue is preferably —$CH_2$—$CH_2$—.

An acyl group such as $R_5$, $R_6$, $R_8$ and $R_9$ in A can for example be an $R_{12}$CO— group in which $R_{12}$ is H, $C_{1-4}$alkyl, $C_{2-4}$alkenyl, $C_{3-6}$cycloalkyl or benzyl, and methyl or ethyl.

When $R_{4a}$ or $R_{11}$ in A is benzyl substituted on the aromatic ring, the benzene ring can be substituted as indicated above for $ZZ_a$.

According to a preferred variant of the invention, the somatostatin agonist analogues are compounds of general formula (II)

in which R is $NR_{10}R_{11}$—$C_{2-6}$alkylene or guanidine-$C_{2-6}$alkylene, and each of $R_{10}$ and $R_{11}$ is independently H or $C_{1-4}$alkyl or are pharmaceutically acceptable salts or protected forms of compounds of general formula (II).

Preferably, R is $NR_{10}R_{11}$—$C_{2-6}$alkylene. The preferred compounds of general formula (II) are those such that R is 2-aminoethyl (and in particular the peptide SOM 230 of the formula cyclo[{4—($NH_2$—$C_2H_4$—NH—CO—O—)Pro}-Phg-DTrp-Lys-Tyr(4-Bzl)-Phe] the structure of which is reproduced below).

By "protected form" of a compound of general formula (I) or (II), is meant in the present application a somatostatin analogue in which at least one of the amino groups is protected and the deprotection of which (which preferably is itself carried out in physiological medium) leads to a compound of general formula (I) or (II). Suitable protective groups for amino groups are for example those described in *Protective Groups in Organic Synthesis*, T. W. Greene, J. Wiley & Sons NY (1981), 219-287. An example of such a protective group for an amino group is the acetyl group.

Among the somatostatin agonist analogues which can be used according to the invention, lanreotide, octreotide, vapreotide, SOM 230 (see structure below), MK-678 (peptide of structure cyclo(N-Me-Ala-Tyr-D-Trp-Lys-Val-Phe)), BIM-23190 (peptide of structure N-hydroxyethylpiperazinyl-acetyl-D-Phe-cyclo[Cys-Tyr-D-Trp-Lys-Abu-Cys]-Thr-$NH_2$), BIM-23197 (peptide of structure Hepes-D-Phe-cyclo[Cys-Tyr-D-Trp-Lys-Abu-Cys]-Thr-$NH_2$ in which Abu represents aminobutyric acid), BIM-23268 (peptide of structure cyclo[Cys-Phe-Phe-D-Trp-Lys-Thr-Phe-Cys]-$NH_2$), PTR-3173 (see structure below), TT-232 (of structure D-Phe-cyclo[Cys-D-Trp-Lys-Cys]-Thr-$NH_2$), and their pharmaceutically acceptable salts can more particularly be mentioned; the synthetic peptide of formula c[Tic-Tyr-DTrp-Lys-Abu-Phe] and its pharmaceutically acceptable salts can also be mentioned; finally the KE 108 peptide of formula $Tyr^0$-(cyclo-D-Dab-Arg-Phe-Phe-D-Trp-Lys-Thr-Phe) described in particular in Reubi et al., *Eur. J. Pharmacol.* (2002), 456, 45-49, can be mentioned. The use of lanreotide, octreotide or one of their pharmaceutically acceptable salts, and more particularly lanreotide or one of its pharmaceutically acceptable salts is quite particularly preferred.

SOM 230

PTR 3173

In a similar way to the compounds of general formula (I) or (II), the above-mentioned peptides can also be presented in a protected form. The definition of the protected form given above for the compounds of general formulae (I) or (II) is applicable *mutatis mutandis*.

According to a preferred variant of the invention, the patients for whom the medicament based on somatostatin or a somatostatin agonist analogue mentioned above is intended are women having an early menopause risk factor, and in particular women with a family history of early menopause. According to a particular variant of the invention, the patients for whom the medicament based on somatostatin or somatostatin agonist analogue mentioned above is intended are women who have an X chromosome microdeletion or a partial Turner syndrome.

The second benefit of the discovery mentioned above resides in the possibility of preparing a medicament based on a somatostatin antagonist analogue in order to accelerate the start of growth of the quiescent follicles. In fact, one couple in six of those who wish to achieve a pregnancy has difficulty conceiving. Although there are many causes, two types of treatment have emerged and are commonly used in human medicine for the treatment of sterility. These treatments, also called "Medically Assisted Procreation" (MAP), consist firstly of inducing the simultaneous growth of several preovulatory follicles. This makes it possible to obtain several mature oocytes, and therefore several embryos, and thus to increase the chances of conception. This is achieved by the administration of one or more medicaments stimulating the pituitary secretion of gonadotropins (FSH and LH), such as an anti-estrogen (for example clomiphene citrate or tamoxifen) or an aromatase inhibitor (for example letrozole, anastrazole or exemestane). The simultaneous growth of several preovulatory follicles can also be induced by the administration of a preparation of human FSH (extractive or recombinant) combined or not combined with LH. When the follicles have reached a preovulatory size, depending on the cause of sterility, two treatment options exist. The first is to carry out an intrauterine insemination (IUI) and the second is to remove the oocytes from the ovary by aspiration of the follicles (between 5 and 15 oocytes) and to carry out an insemination in the laboratory (in vitro), either by simple coincubation of the oocytes with the partner's sperm (IVF) or by microinjection of sperm directly into the oocyte (ICSI). It is essential to obtain several mature oocytes in order to optimize the success rates (pregnancy rates) obtained with these treatments; however in certain women, despite appropriate ovarian stimulation, the number of oocytes obtained is low or even equal to one. This difficulty in responding to the stimulating treatment is a result of the limited number of growing follicles present in the ovaries of these patients. It is therefore of considerable therapeutic benefit to be able to activate follicles of the ovarian reserve and make them enter the growth phase.

Another subject of the present invention is the use of a somatostatin antagonist analogue for preparing a medicament intended to accelerate the start of growth of the quiescent follicles in non-menopausal women.

The administration of such a medicament over a period of 1 to 12 months in women leads to an increase in the number of follicles in the growth phase and which are therefore able to be stimulated with the standard treatments in order to reach the stage of preovulatory follicles.

Another application of the ability of the somatostatin antagonist analogues to induce early follicle growth is their in vitro use in follicle cultures for the production of mature oocytes intended for fertilization. The somatostatin antagonist analogue is added to the culture media used to support in vitro follicle development. The invention therefore also relates to the corresponding media comprising a somatostatin antagonist analogue. Moreover, the ability of the somatostatin antagonist analogues to induce early follicle growth can also be used in the field of toxicological analyses. In particular, during tests of the effect of new chemical entities on follicle growth, the addition to the follicle sample of a somatostatin antagonist analogue makes it possible to accelerate follicle growth and thus to more easily observe any effect of slowing of said growth caused by said novel chemical entities.

The somatostatin antagonist analogue can be a cyclic or non cyclic polypeptide, a fusion or recombination protein, a non-peptide chemical entity (i.e. a peptidomimetic) or also a "SS-like" peptide such as corticostatin. The antagonist analogues to be used must have a high affinity for the SST receptor and inhibit the functional activity of SST14 or SST28 such as the inhibition of the secretion of growth hormone by somatotrope cells of the pituitary and/or the inhibition of the in vitro proliferation of pituitary adenoma cells. Preferably, the somatostatin antagonist analogue has a high affinity for all or at least 2 or 3 of the sub-types of SST receptors or a greater affinity for at least one of the sub-types 1, 2, 3, 4 and 5 (for example for sub-type 2).

A somatostatin antagonist analogue which can be used for the preparation according to the invention can for example be a peptide of general formula $$A^1\text{-cyclo}\{D\text{-Cys-}A^2\text{-D-Trp-}A^3\text{—}A^4\text{-Cys}\}\text{-}A^5\text{—}Y^1 \quad (III)$$

in which:

$A^1$ is an optionally substituted aromatic α-amino acid;

$A^2$ is an optionally substituted aromatic α-amino acid;

$A^3$ is Dab, Dap, Lys or Orn;

$A^4$ is β-Hydroxyvaline, Ser, Hser, or Thr;

$A^5$ is an optionally substituted aromatic D- or L-α-amino acid; and

$Y^1$ is OH, $NH_2$ or $NHR^1$, $R^1$ being $(C_{1-6})$alkyl;

each optionally substituted aromatic α-amino acid being optionally substituted with one or more substituents independently chosen from the group comprising a halogen atom and the groups $NO_2$, OH, CN, $(C_{1-6})$alkyl, $(C_{2-6})$alkenyl, $(C_{2-6})$alkynyl, $(C_{1-6})$alkoxy, Bzl, O-Bzl and $NR^9R^{10}$, $R^9$ and $R^{10}$ each being independently H, O, or $(C_{1-6})$alkyl; and each nitrogen atom with a peptide amide bond and the amino group of $A^1$ being optionally substituted with a methyl group, it being understood that there is at least one such methyl group in a peptide of general formula (III);

or a pharmaceutically acceptable salt of a peptide of general formula (III).

By "aromatic α-amino acid" is meant an amino acid residue of formula in which $Z_1$ is a radical containing an aromatic ring and $Z_2$ is a hydrogen atom or a radical containing an aromatic ring. Examples of such radicals containing an aromatic ring include, but are not limited to, a benzene or pyridine ring and the following structures with or without one or more X substituents on the aromatic ring (X being, independently each time that it occurs, a halogen atom, $NO_2$, $CH_3$, $OCH_3$, $CF_3$ or OH):

Other examples of an "aromatic α-amino acid" according to the invention are substituted His, such as MeHis, His (τ-Me) or His (π-Me).

Other somatostatin antagonist analogues have been described in particular in the patent applications PCT WO 98/08528, WO 98/08529, WO 98/24807, WO 98/44921, WO 98/44922, WO 98/45285 and WO 99/22735, or also in the patents U.S. Pat. Nos. 6,387,932, 6,262,229, 6,063,796, 6,057,338, 6,025,372, 5,925,618, 5,846,934 and 4,508,711.

Among the somatostatin antagonist analogues which can be used according to the invention and their pharmaceutically acceptable salts, there may more particularly be mentioned:

the following peptides of general formula (III):

Cpa-cyclo[D-Cys-Pal-D-Trp-N-Me-Lys-Thr-Cys]-D-Trp-$NH_2$;

Cpa-cyclo[D-Cys-Tyr-D-Trp-N-Me-Lys-Thr-Cys]-Nal-$NH_2$;

Cpa-cyclo[D-Cys-Pal-D-Trp-N-Me-Lys-Thr-Cys]-Nal-$NH_2$;

the peptide known by the code name AC-178,335 (of structure acetyl-D-His-D-Phe-D-Ile-D-Arg-D-Trp-D-Phe-$NH_2$);

the octapeptide known by the code name ODN-8 (cf. FIG. 1 of *Proc. Natl. Acad. Sci.* USA (2000), 97(25), 13973-13978);

ODN-8 the peptide known by the code name SB-710411 (of structure Cpa-cyclo[D-Cys-Pal-D-Trp-Lys-Val-Cys]-Cpa-amide);
the peptide known by the code name BIM-23056 (of the structure represented below);
the compound known by the code name BN-81674 (of the structure represented below);
the compound known by the code name SRA-880 (of the structure represented below);
and their pharmaceutically acceptable salts.

In a similar way to the compounds of general formula (I) or (II), the above-mentioned peptides (including those corresponding to general formula (III)) can also be presented in a protected form. The definition of the protected form given above for the compounds of general formulae (I) or (II) is applicable *mutatis mutandis*.

By somatostatin agonist analogue is meant in the present application a compound for which the effective dose $DE_{50}$ determined in the test of the agonist effect described below is less than or equal to 1 μM for at least one of the somatostatin sub-receptors.

By somatostatin antagonist analogue is meant in the present application a compound for which the effective dose $DE_{50}$ determined in the test of the antagonist effect described below is less than or equal to 1 μM for at least one of the somatostatin sub-receptors.

By pharmaceutically acceptable salt is meant in particular in the present application addition salts with inorganic acids such as hydrochloride, hydrobromide, hydroiodide, sulphate, phosphate, diphosphate and nitrate or with organic acids such as acetate, maleate, fumarate, tartrate, succinate, citrate, lactate, methanesulphonate, p-toluenesulphanate, pamoate and stearate. Also included in the field of the present invention, when they can be used, the salts formed from bases such as sodium or potassium hydroxide. For other examples of pharmaceutically acceptable salts, reference can be made to "Salt selection for basic drugs", *Int. J Pharm.* (1986), 33, 201-217.

According to the present invention, the pharmaceutical preparations containing somatostatin or one of its agonist or antagonist analogues applicable in this invention can be administered by parenteral route (subcutaneous, intramuscular, intraperitoneal, intravenous, or in an implant), by oral, vaginal, rectal, nasal, sublingual or transdermal route. The vaginal route is preferred because it allows effective concentrations of the active ingredient to be delivered to the ovary while minimizing systemic exposure. The somatostatin or the somatostatin analogue used is formulated with the necessary excipients known to a person skilled in the art, in order to allow an effective and reproducible administration for each administration route.

The dose of a product according to the present invention, intended for the treatment of the above-mentioned diseases or problems, varies according to the method of administration, the age and body weight of the subject to be treated as well as the condition of the subject, and the final decision is made by the attending doctor or vet. Such a quantity determined by the attending doctor or vet is called "therapeutically effective quantity" here.

The following typical situations for a use according to the invention could however be envisaged:

A patient of approximately 20 to 25 years of age (for example) has a partial Turner syndrome through X chromosome microdeletion. Her ovarian function is apparently normal with regular ovulatory cycles. Her FSH serum level is slightly higher during the luteal-follicular transition period (for example FSH=approximately 9.2 IU/litre). The ovarian ultrasound carried out by trans-vaginal route shows ovaries of normal volume with a slightly reduced number of antral follicles. Considering the high risk that she will have early menopause, the patient is treated with lanreotide acetate at a dose of 120 mg/months (Somatuline® Autogel® 120 mg, Beaufour Ipsen Pharma, France). The treatment is discontinued after several years when the patient wishes to conceive.

A patient of approximately 35 to 40 years of age has had primary sterility for several years. Assessment of the couple produced a diagnosis of sterility of tubal origin, very probably resulting from a history of peritonitis. The menstrual cycles are ovulatory and the FSH serum level is slightly higher during the luteal-follicular transition period (for example FSH=approximately 11.4 IU/L). The ovarian ultrasound carried out by trans-vaginal route shows ovaries with a slightly reduced volume with a reduced number of antral follicles (approximately 3 per ovary). A diagnosis of reduction of the ovarian reserve is made. An in vitro fertilization treatment is recommended and the patient undergoes ovarian stimulation treatment with daily injection of 225 units of recombinant FSH. On the $6^{th}$ day of stimulation, an ovarian ultrasound shows a single growing follicle of 14 mm in the right ovary. The dose of FSH is doubled and the patient is seen again 2 days later. A single 18-mm follicle is observed, which confirms a reduction in the ovarian reserve. The treatment is discontinued. After return of a spontaneous cycle, a treatment by daily administration of a somatostatin antagonist analogue is initiated. During this treatment, the number of antral follicles present in each ovary is assessed by ultrasound at the start of each menstrual cycle. After 4 months of treatment, the number of antral follicles is on average approximately 6 per ovary and the serum FSH has been reduced. A stimulation by recombinant FSH is initiated, multiple follicular development is obtained, and a standard in vitro fertilization procedure is carried out.

A patient with polycystic ovary syndrome has very irregular periods, absence of ovulation, excessive weight and cutaneous signs of androgen excess such as acne and hirsutism. When the pelvis is examined by ultrasound, the endometrium is hyperplastic, the ovaries have increased volume, an increased stroma, and more than 10 antral follicles per ovarian section. No follicle has a diameter greater than 10 mm. The patient is treated with lanreotide acetate at a dose of 120 mg/month (Somatuline® Autogel® 120 mg, Beaufour Ipsen Pharma, France). After 3 months of treatment, the patient has spontaneous periods. In the $4^{th}$ month of treatment, the ultrasound of the ovaries indicates a reduction in ovarian volume and in the number of antral follicles. One 16 mm follicle is observed. During the $5^{th}$ and 6th months of treatment, the patient has regular periods and her temperature curve is biphasic, suggesting an ovulation. In the $8^{th}$ month of treatment, the patient does not have a period and a pregnancy test is positive. The treatment with lanreotide acetate is discontinued.

Particular Abbreviations and Definitions Used in the Present Application:

The abbreviations of the common amino acids are in accordance with the IUPAC-IUB recommendations. Moreover, the definitions for certain abbreviations used in the present application are as follows:

Abu=α-aminobutyric acid;
Aib=α-aminoisobutyric acid;
β-Ala =β-alanine;
Amp=4-aminophenylalanine;
Ava=5-aminovaleric acid;
Bzl=benzyl;
Cha=cyclohexylalanine;
Cpa=3-(4-chlorophenyl)alanine;
Dab=2,4-diaminobutyric acid;
Dap=2,3-diaminopropionic acid;
Dip=3,3'-diphenylalanine;
GABA=γ-aminobutyric acid;
HSer=homoserine;
1-Nal=3-(1-naphthyl)alanine;
2-Nal=3-(2-naphthyl)alanine;
Nle=norleucine;
Nva=norvaline;
2-Pal=3-(2-pyridyl)alanine;
3-Pal=3-(3-pyridyl)alanine;
4-Pal=3-(4-pyridyl)alanine;
Phg=—HN—CH($C_6H_5$)—CO—
Tfm=trifluoromethyl;
TfmA=4-trifluoromethylphenyl-alanine;
Tic=1,2,3,4-tetrahydroisoquinoline-3-carboxylic acid.

Moreover, NMeLys represents the N-methyl-lysine, in which the nitrogen of the peptide bond is methylated (and not the nitrogen of the side chain of the lysine).

Finally, Tyr(I) represents an iodized tyrosine residue (for example 3-1-Tyr, 5-I-Tyr, 3,5-I-Tyr) in which the iodine atom can be a radioactive isotope, for example $I_{125}$, $I_{127}$ or $I_{131}$.

Moreover, the term "approximately" refers to an interval around the value considered. As used in the present application, "approximately X" means an interval of X less 10% of X to X plus 10% of X, and preferably an interval of X less 5% of X to X plus 5% of X.

Preparation of the Peptides of General Formula (I):

The peptides of general formulae (I) and (II) mentioned above and their synthesis are described for instance in the patent applications PCT WO 97/01579 and WO 02/10192.

The peptides of general formula (III) mentioned above and their synthesis are described in the patent application PCT WO 02/072602.

Unless they are otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are given in order to illustrate the above procedures and must in no event be considered to be a limit to the scope of the invention.

EXAMPLES

Example 1

Ovaries of adult ewes are collected immediately after slaughter. The ovaries are placed in an organ transport medium without serum (X-vivo, Bio Whittaker, Walkersville, Md., USA) at 10° C. and transported to the laboratory. Approximately 1 h after removal, the cortex is isolated from the medulla then fractionated into slices of 2 mm thickness (1 cm$^2$, average weight of 212 mg) after rinsing in new X-vivo. The cortex fragments are cultured in an oven under 5% oxygen for 10 days in well plates in the presence of DMEM. The medium is changed every 2 days.

Figure 1:
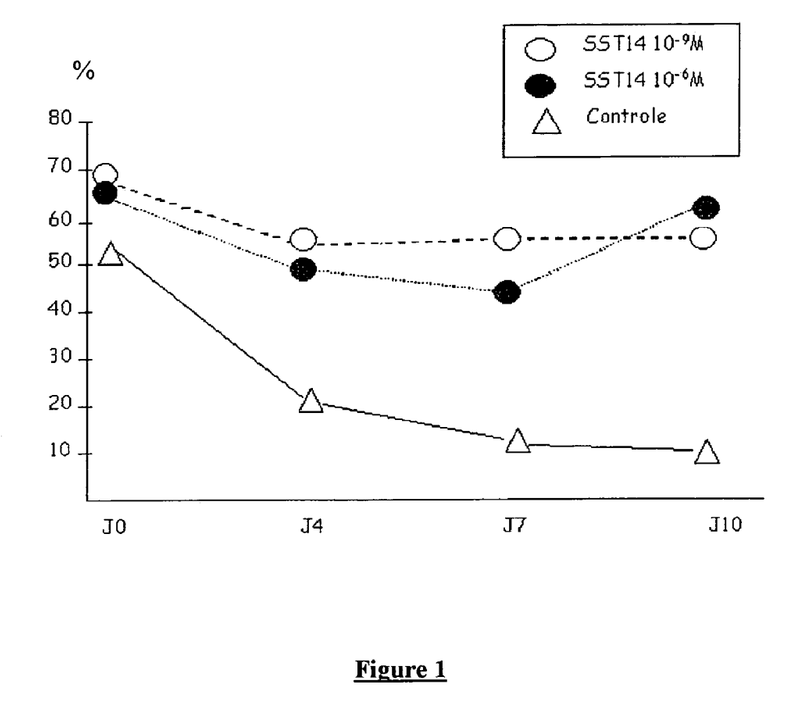
FIG. 1 represents the proportions of dormant follicles during a period of 10 days of culture of an ovarian cortex of a ewe in the presence or absence (control) of somatostatin (SST14). These proportions are measured for each sample tested on the day of the start of the experiment (D0), on the 4$^{th}$ day (D4), on the 7$^{th}$ day (D7) and on the 10$^{th}$ day (D10).
Figure 2:
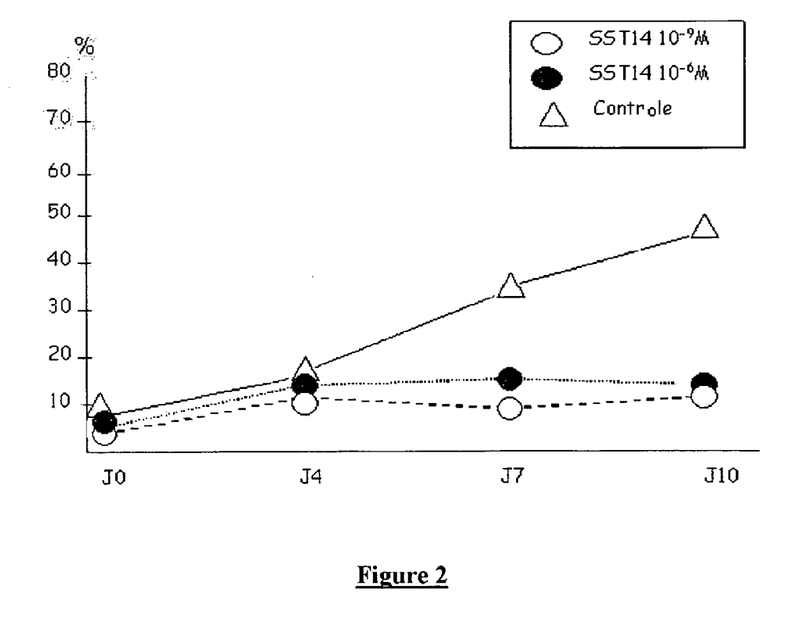
FIG. 2 represents the proportions of primary follicles during a period of 10 days of culture of an ovarian cortex of a ewe in the presence or absence (control) of somatostatin (SST14). These proportions are measured for each sample tested on the day of the start of the experiment (D0), on the 4$^{th}$ day (D4), on the 7$^{th}$ day (D7) and on the 10$^{th}$ day (D10).

In the control fragments (incubated in the absence of SST) the primordial follicles gradually progress to the state of follicles at the start of growth (see FIGS. 1 and 2). The addition of SST14 at concentrations varying between $10^{-9}$ M and $10^{-6}$ M very significantly inhibits the start of growth of the primordial follicles as is shown by the maintenance over time of the number of primordial follicles (cf. FIG. 1) and the absence of increase in the number of primary follicles (cf. FIG. 2).

Example 2

The procedure used is the same as for Example 1, except that the somatostatin is replaced with one of its agonist analogues, namely the synthetic peptide of formula c[Tic-Tyr-DTrp-Lys-Abu-Phe] (hereafter $AG_1$ peptide).

Figure 3:
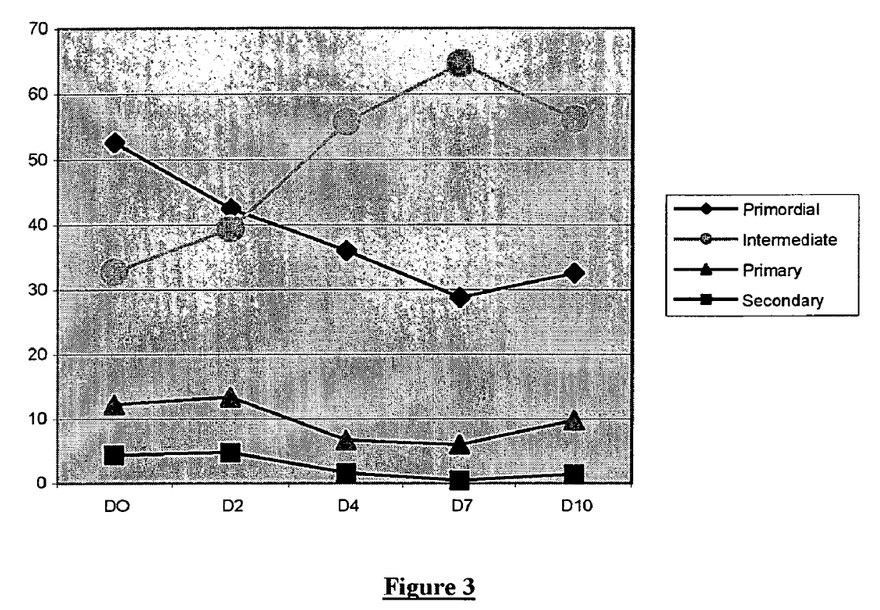
FIG. 3 represents the proportions of primordial, intermediate, primary and secondary follicles during a period of 10 days of culture of an ovarian cortex of a ewe in the absence of agonist or somatostatin antagonist analogue. These proportions are measured for each sample tested on the day of the start of the experiment (D0), on the 4$^{th}$ day (D4), on the 7$^{th}$ day (D7) and on the 10$^{th}$ day (D10).
Figure 4:
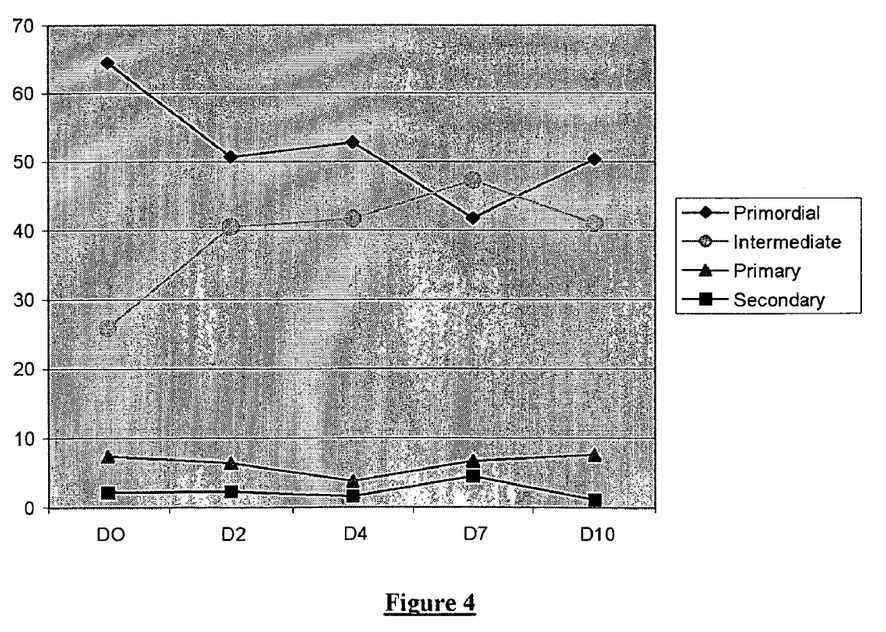
FIG. 4 represents the proportions of primordial, intermediate, primary and secondary follicles during a period of 10 days of culture of an ovarian cortex of a ewe in the presence or absence of a somatostatin agonist analogue, the synthetic peptide of formula c[Tic-Tyr-DTrp-Lys-Abu-Phe] ($AG_1$ peptide). These proportions are measured for each sample tested on the day of the start of the experiment (D0), on the 4$^{th}$ day (D4), on the 7$^{th}$ day (D7) and on the 10$^{th}$ day (D10).

In the control fragments (incubated in the absence of $AG_1$ peptide) the primordial follicles gradually progress to the state of follicles at the start of growth (cf. FIG. 3). The addition of $AG_1$ peptide at a concentration of $10^{-9}$ M very significantly inhibits the start of growth of the primordial follicles as is shown by the maintenance over time of the number of primordial follicles and the absence of increase in the number of primary follicles (cf. FIG. 4).

Example 3

The procedure used is the same as for Example 1, except that the somatostatin is replaced by one of its antagonist analogues, namely the synthetic peptide of formula Cpa-c(DCys-3-Pal-DTrp-NMeLys-Thr-Cys)-2-Nal-NH$_2$ (hereafter $ANT_1$ peptide).

Figure 5:
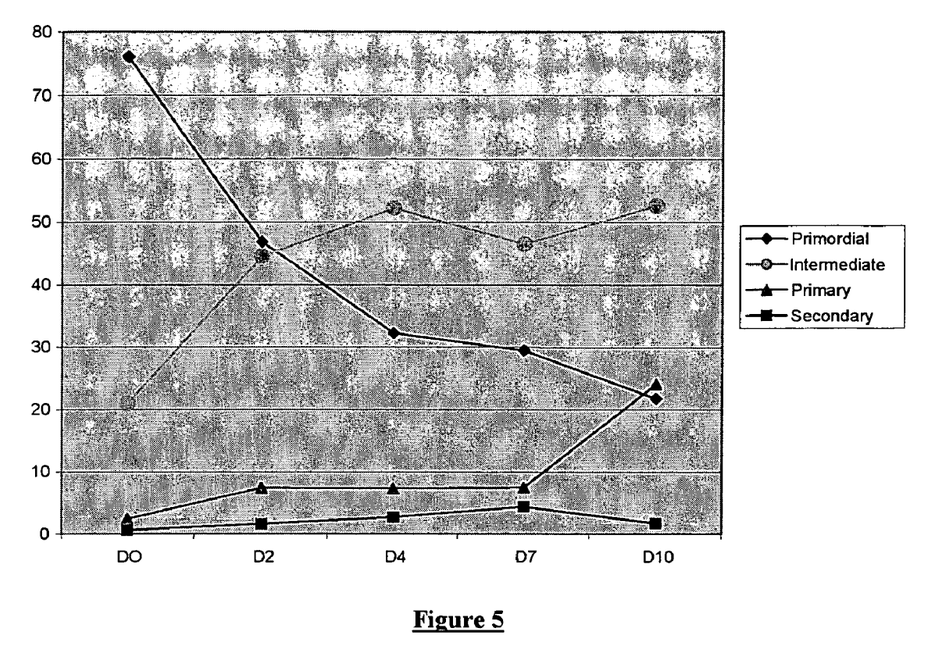
FIG. 5 represents the proportions of primordial, intermediate, primary and secondary follicles during a period of 10 days of culture of an ovarian cortex of a ewe in the presence or absence of a somatostatin antagonist analogue, the synthetic peptide of formula Cpa-c(DCys-3-Pal-DTrp-NMeLys-Thr-Cys)-2-Nal-NH$_2$ ($ANT_1$ peptide). These proportions are measured for each sample tested on the day of the start of the experiment (D0), on the 4th day (D4), on the 7th day (D7) and on the 10th day (D10).

In the control fragments (incubated in the absence of $ANT_1$ peptide) the primordial follicles gradually progress to the state of follicles at the start of growth (cf. FIG. 3). It is observed that the addition of $ANT_1$ peptide at a concentration of $10^{-6}$ M accentuates the start of growth of the primordial follicles (cf. FIG. 5).

TESTS FOR DETERMINATION OF THE AGONIST OR AMTAGONIST EFFECT OF A SOMATOSTATIN ANALOGUE

Inhibition of the Intracellular Production of cAMP

CHO-K1 cells expressing the sub-types of human somatostatin (SRIF-14) receptors are cultured in 24-well plates in an RPMI 1640 medium containing 10% foetal calf serum. The medium is changed the day before the experiment.

The cells at a rate of $10^5$ cells/well are washed twice with 0.5 ml of new RPMI medium comprising 0.2% BSA completed with 0.5 mM of 3-isobutyl-1-methylxanthine (IBMX) and incubated for approximately 5 minutes at approximately 37° C. The production of cyclic AMP is stimulated by the addition of 1 mM of forskolin (FSK; supplier: Sigma Chemical Co., St. Louis, Mo., USA) for 15-30 minutes at approximately 37° C.

Determination of the Agonist Effect of a Somatostatin Analogue

The agonist effect of a somatostatin analogue is measured by the simultaneous addition of FSK (1 μM) and the analogue to be tested ($10^{-10}$ M to $10^{-5}$ M).

The reaction medium is eliminated and 200 ml of HCI 0.1 N are added. The quantity of cAMP is measured by a radio-immunoassay (Kit FlashPlate SMP001A, New England Nuclear, Boston, USA).

Determination of the Antagonist Effect of a Somatostatin Analogue

The antagonist effect of a somatostatin analogue is measured by the simultaneous addition of FSK (1 μM), SRIF-14 (1 to 10 nM) (supplier: Bachem, Torrence, Calif., USA) and the analogue to be tested ($10^{-10}$ M to $10^{-5}$ M).

The reaction medium is eliminated and 200 ml of HCI 0.1 N are added. The quantity of cAMP is measured by a radio-immunoassay (Kit FlashPlate SMP001A, New England Nuclear, Boston, USA).

The invention claimed is:

1. A method of accelerating the start of growth of quiescent follicles in non-menopausat women comprising administering to a patient in need thereof a medicament comprising a somatostatin antagonist analog having the general formula (III)

$$A^1\text{-cyclo}\{D\text{-Cys-}A^2\text{-D-Trp-}A^3\text{-}A^4\text{-Cys}\}\text{-}A^5\text{-Y}^1 \qquad (III)$$

in which:
- $A^1$ is an optionally substituted aromatic α-amino acid;
- $A^2$ is an optionally substituted aromatic α-amino acid;
- $A^3$ is Dab, Dap, Lys, or Orn;
- $A^4$ is β-Hydroxyvaline, Ser, Hser, or Thr;
- $A^5$ is an optionally substituted aromatic D- or L- α-amino acid; and
- $Y^1$ is OH, $NH_2$ or $NHR^1$, $R^1$ is $(C_{1-6})$alkyl;
- each aromatic α-amino acid being optionally substituted with one or more substituents independently selected from a halogen atom, $NO_2$, OH, CN, $(C_{1-6})$ alkyl, $(C_{2-6})$ alkenyl, $(C_{2-6})$ alkynyl, $(C_{1-6})$ alkoxy, Bzl, O-Bzl or $NR^9R^{10}$, wherein $R^9$ and $R^{10}$ are each independently H, O, or $(C_{1-6})$ alkyl; and
- each nitrogen atom of a peptide amide bond and the amino group of $A^1$ are optionally substituted with a methyl group, with the proviso that there is at least one said methyl group in a peptide of general formula (III);

or a phannaceutic ally acceptable salt or protected form, or a combination thereof.

2. The method of claim 1, wherein $A^1$ is Cpa, $A^2$ is Pal, $A^3$ is Lys, $A^4$ is Thr, and $A^5$ is Nal.

3. The method of claim 2, wherein the somatostatin antagonist analog is Cpa-cyclo(DCys-3-Pal-DTrp-NMeLys-Thr-Cys)-2-Nal-$NH_2$.

4. The method of claim 1, wherein the somatostatin antagonist analog is:

5. A method of accelerating the start of growth of quiescent follicles in non-menopausal women comprising administering to a patient in need thereof a medicament comprising a somatosratin antagonist analog selected from the group consisting of:

Cpa-cyclo[D-Cys-Pal-D-Trp-N-Me-Lys-Thr-Cys]-D-Trp-$NH_2$;

Cpa-cyclo[D-Cys-Tys-D-Trp-N-Me-Lys-Thr-Cys]-Nal-$NH_2$;

Cpa-cyclo[D-Cys-Pal-D-Trp-N-Me-Lys-Thr-Cys]-Nal-$NH_2$; acetyl-D-His-D-Phe-D-Ile-D-Arg-D-Trp-D-Phe-$NH_2$;

Cpa-cyclo[D-Cys-Pal-D-Trp-Lys-Val-Cys]Cpa-amide;

; and combinations thereof; or
a pharmaceutically acceptable salt or protected form, or a combination thereof.

* * * * *

UNITED STATES PATENT AND TRADEMARK OFFICE
CERTIFICATE OF CORRECTION

| | | |
|---|---|---|
| PATENT NO. | : 7,648,961 B2 | Page 1 of 1 |
| APPLICATION NO. | : 10/575236 | |
| DATED | : January 19, 2010 | |
| INVENTOR(S) | : Gougeon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 446 days.

Signed and Sealed this

Twenty-eighth Day of December, 2010

David J. Kappos
*Director of the United States Patent and Trademark Office*